United States Patent [19]
Kopfer

[11] Patent Number: 5,428,411
[45] Date of Patent: Jun. 27, 1995

[54] PROTECTIVE EYEWEAR DEVICE AND LENS THEREFOR

[76] Inventor: Rudolph J. Kopfer, P.O. Box 2894, Ketcham, Id. 83340

[21] Appl. No.: 2,469
[22] Filed: Jan. 8, 1993

Related U.S. Application Data

[60] Division of Ser. No. 601,467, Oct. 23, 1990, Pat. No. 5,191,364, which is a continuation-in-part of Ser. No. 405,421, Sep. 11, 1989, abandoned.

[51] Int. Cl.$^6$ ............................ G02C 3/00; G02C 7/02
[52] U.S. Cl. ................................ 351/62; 351/43; 351/159; 2/436
[58] Field of Search ............... 351/41, 63, 62, 118, 351/43, 159, 115; 2/436, 446, 452, 437, 439, 435; 359/795

[56] References Cited

U.S. PATENT DOCUMENTS

| | | | |
|---|---|---|---|
| Re. 12,924 | 3/1909 | Cover | 2/440 |
| D. 293,504 | 1/1988 | Specht et al. | D16/107 |
| D. 295,533 | 5/1988 | Wichers | D16/102 |
| 1,031,859 | 7/1912 | Malcolm | 2/439 |
| 1,168,581 | 1/1916 | Troppman | 2/440 |
| 1,433,676 | 10/1922 | Cover | 2/440 |
| 1,478,818 | 12/1923 | Cover | 2/440 |
| 1,562,350 | 11/1925 | Luckey | 52/172 |
| 1,669,229 | 5/1928 | Cook | 2/440 |
| 1,677,747 | 7/1928 | Cook | 2/440 |
| 1,720,814 | 7/1929 | Baker | 2/440 |
| 1,741,427 | 12/1929 | Meyrowitz | 2/440 |
| 1,754,694 | 4/1930 | Neuwirth | 2/440 |
| 1,846,679 | 2/1932 | Fischer | 2/440 |
| 1,853,872 | 4/1932 | Meyrowitz | 2/440 |
| 1,936,746 | 11/1933 | Baker | 2/14 |
| 1,989,876 | 2/1935 | Meyrowitz | 2/14 |
| 2,002,543 | 5/1935 | Meyrowitz | 2/14 |
| 2,007,186 | 7/1935 | Farrell | 2/14 |
| 2,026,435 | 12/1935 | Ratti | 2/14 |
| 2,088,262 | 7/1937 | Grano | 351/43 |
| 2,182,104 | 12/1939 | Wilen et al. | 2/14 |
| 2,321,159 | 6/1943 | Ryan | 2/441 |
| 2,364,584 | 12/1944 | Malcolm | 2/14 |
| 2,387,821 | 10/1945 | Baratelli et al. | 2/14 |
| 2,446,048 | 7/1948 | Kimball | 2/14 |
| 2,526,181 | 10/1950 | Wilen | 2/14 |
| 2,608,687 | 9/1952 | Ellis | 2/14 |
| 2,846,684 | 8/1958 | Hill | 2/14 |
| 2,865,253 | 12/1958 | Thielens | 359/356 |
| 3,040,616 | 6/1962 | Simpson | 359/481 |
| 3,377,626 | 4/1968 | Smith | 2/435 |
| 3,419,909 | 1/1969 | Spain | 2/174 |
| 3,556,644 | 1/1971 | Stahl | 351/118 |
| 3,591,864 | 7/1971 | Allsop | 2/436 |
| 3,865,619 | 2/1975 | Pennewiss et al. | 117/138.8 |
| 3,867,175 | 2/1975 | Dornte | 117/47 A |
| 4,099,858 | 7/1978 | Land | 351/62 |
| 4,264,987 | 5/1981 | Runckel | 2/428 |
| 4,405,212 | 9/1983 | Cooper | 351/43 |
| 4,414,693 | 11/1983 | Brody | 2/435 |
| 4,468,819 | 9/1984 | Ohno | 2/430 |
| 4,544,245 | 10/1985 | Stansbury, Jr. | 351/120 |
| 4,547,049 | 10/1985 | Cotie | 351/159 |
| 4,654,899 | 4/1987 | Harris | 2/436 |
| 4,707,863 | 11/1987 | McNeal | 2/436 |
| 4,717,249 | 1/1988 | Fischer | 351/43 |
| 4,741,611 | 5/1988 | Burns | 351/44 |
| 4,785,481 | 11/1988 | Palmer, III et al. | 2/436 |
| 4,792,221 | 12/1988 | Parks et al. | 351/120 |
| 4,867,553 | 9/1989 | Frieder | 351/172 |
| 4,877,320 | 10/1989 | Holden | 351/44 |
| 4,955,708 | 9/1990 | Kahaney | 351/44 |
| 5,018,223 | 5/1991 | Dawson et al. | 351/62 X |
| 5,191,364 | 3/1993 | Kopfer | 351/62 |

FOREIGN PATENT DOCUMENTS

| | | |
|---|---|---|
| 321010 | 7/1902 | France . |
| 324973 | 10/1902 | France . |
| 2130907 | 10/1972 | France . |
| 56-133716 | 10/1981 | Japan . |
| 127410 | 5/1919 | United Kingdom . |
| 364970 | 1/1932 | United Kingdom . |

Primary Examiner—William L. Sikes
Assistant Examiner—David R. Parsons
Attorney, Agent, or Firm—Haverstock, Medlen & Carroll

[57] ABSTRACT

Protective eyewear for sports activities and the like having a resilient rigid frame is disclosed. Included is a sealing area around the eyes having a web which diverges outwardly in every direction toward the lens frame. The frame is curvedly contoured around the face of the user and in conjunction with the diverging web, provides both maximum eye protection and peripheral visibility. A semi-rigid frame provides for temple mounting and obviates the need for around-the-head straps.

26 Claims, 5 Drawing Sheets

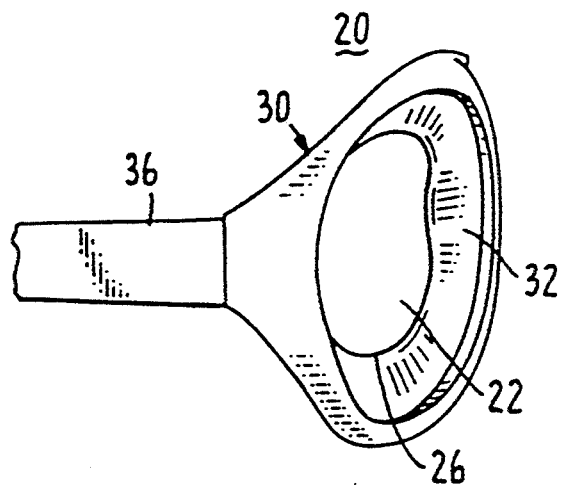
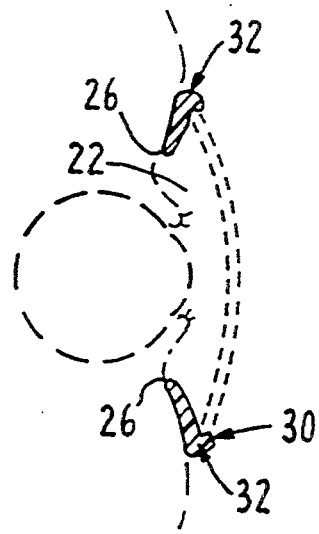
FIG. 5
FIG. 6
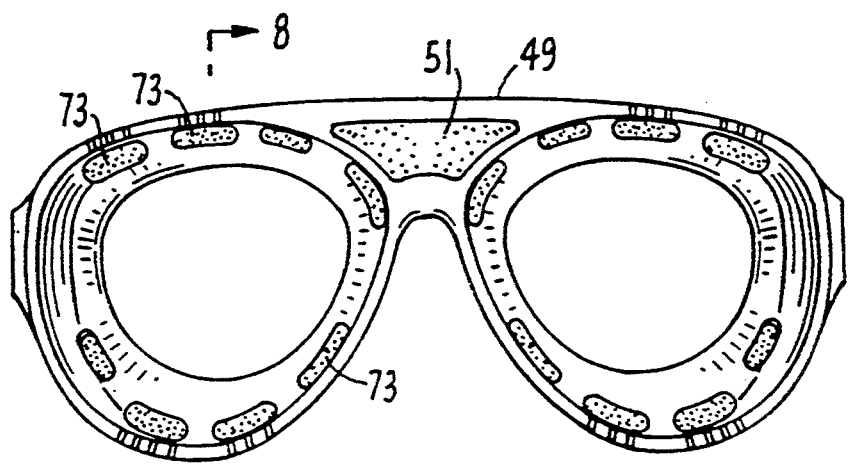
FIG. 7
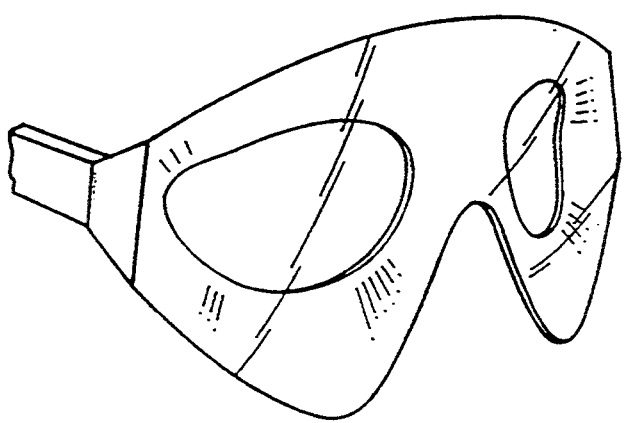
FIG. 9
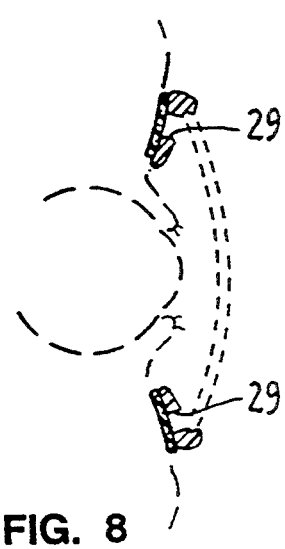
FIG. 8

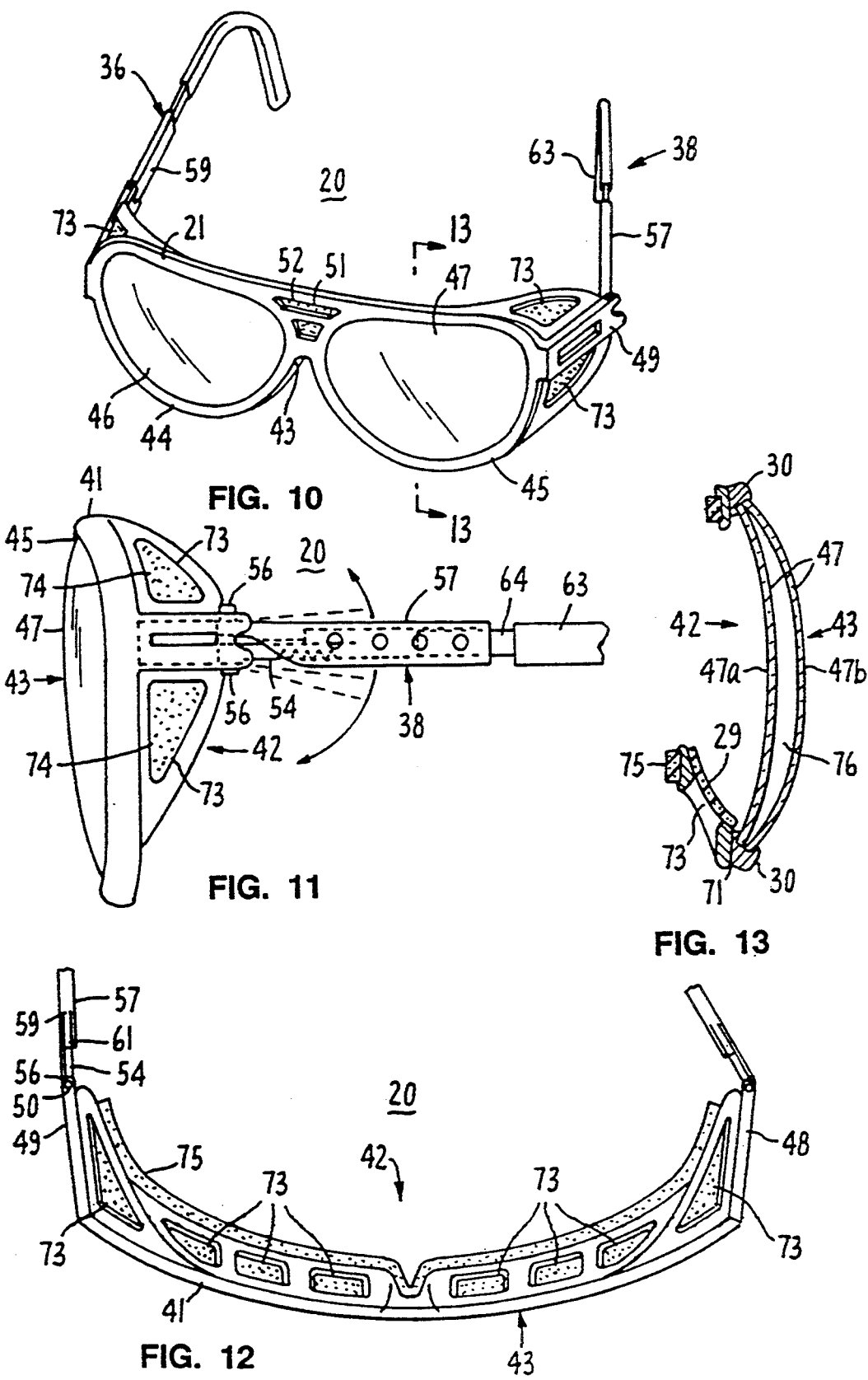

PROTECTIVE EYEWEAR DEVICE AND LENS THEREFOR

This application is a division of U.S. patent application Ser. No. 07/601,467 filed on Oct. 23, 1990, now U.S. Pat. No. 5,191,364, which is a continuation-in-part of U.S. patent application Ser. No. 07/405,421 filed Sep. 11, 1989 (now abandoned).

TECHNICAL FIELD OF THE INVENTION

This invention relates to protective eyewear for use in sports and the like. The eyeglasses are configured in a wrap around design. The eye support is contoured to snugly fit the eye orbital and diverge therefrom outward to the lens support area of the frame to provide for maximum peripheral vision of at least 140 degrees.

BACKGROUND OF THE INVENTION

This invention relates to protective eyewear for use in sports and the like. The device which is the subject of this application is adapted to provide the prophylactic eye protection of goggles while giving the appearance of light weight, streamlined eye glasses with an unobstructed field of vision.

Many diverse types of sports and other activities of necessity suggest that the participant wear some type of eye protection. Consequently, there are different types of eyeglasses and goggles which are appropriate for each activity. For example, in bad weather snow skiers want eye protection that prevents the penetration of wind, rain, snow, sleet, sand, dirt, dust and peripheral glare into the eyes. In fair weather, the desire for eye protection may be limited to protection against sun glare.

For snow skiing, in the prior art, sunglasses sufficed as eye protection from the sun. Sunglasses were light weight, compact, stylish, easily put on and taken off, and did not obstruct the wearer's field of vision. Sunglasses were attached along the temples, around the ears, and not around the back of the head. Such attachment necessarily required that the frame be at least semi-rigid.

In the prior art protective eyewear goggles were necessary for bad weather. Goggles, however, are large, cumbersome, awkward and difficult to wear. Most skiers, and other sports participants, find this objectionable. Preferable is the unrestraining fit and convenience offered by eye glasses which are lightly retained on the face of the user.

Prior art devices such as those disclosed in U.S. Pat. No. 1,669,229 Cook, U.S. Pat. No. 1,677,747, U.S. Pat. No. 1,936,746 Baker, and U.S. Pat. No. 1,754,694 Neuwirth unsuccessfully attempted to modify eyeglasses to provide all weather goggle-like eye protection while retaining the appearance and advantages of eyeglasses. These prior art devices were fitted with rubber, foam or some other non-rigid substance around the inside perimeter of the eyeglasses in an attempt to form an acceptable seal. However, as the non-rigid material easily deformed, it would not necessarily retain its resiliency and its shape after multiple uses, and would thereby become ineffective after a short period of time. Further, the placement of the non-rigid substance blocked peripheral vision, thereby severely restricting the wearer's field of vision.

Moreover, unlike eyeglasses, goggles are customarily held in place by an elastic or adjustable head band. Goggles use a strap around the wearer's head, as the frame is flexible; goggles do not support temple bars because of their non-rigid frame.

For goggles to create a protective seal, the head band is positioned circumferentially around the back of the wearer's head. The head band is attached, at both ends, to the goggle mask which is bent around the wearer's face. In this manner, goggles provide a larger field of vision and a tight seal against the user's face thereby shielding the user's eyes from the elements.

Although goggles form a shielding seal around the face, goggles are not a preferred form of eyewear; goggles are typically large, non-rigid, bulky, awkward, and uncomfortable to the wearer. These problems are substantially obviated by the present invention, which provides a spectacle like frame with all of the protective benefits of goggles, while not impinging on the wearer's field of vision.

SUMMARY OF THE INVENTION

The present invention overcomes all of the inherent deficiencies and limitations in the prior art devices. The present invention is light weight, aesthetically pleasing, comfortable, and can be used to protect the eyes in any type of weather. It gives the appearance of eyeglasses while offering substantially more eye protection, without diminution in the wearer's field of vision.

The present invention provides a resilient semi-rigid or rigid frame having a sealing area around the eyes with a web which diverges outwardly toward the frame. The frame is curvedly contoured around the face of the user and in conjunction with the diverging web, provides maximum peripheral visibility.

The diverging web of the frame, and/or the inside of the frame, may be provided with a plurality of vent holes to promote the circulation of air and thereby inhibit misting of the inner surface of the lenses. Advantageously, a ram air intake can be provided in the front face of the frame and disposed in the nose bridge area. However, the ram air intake can be located elsewhere on the front of the frame, if desired. The various vent holes and air intakes may also be covered with a thin breathable cellular foam material to further shield the user from the elements.

Accordingly, a lens, or pair of lenses, is secured at the frame. The lens, or pair of lenses, may be of a double-walled construction. Each double-walled construction, having two lenses, may be either separated by an air space or abutted against one another. If an air space is provided, the two lenses may have a different base curve to provide an air space while having a common peripheral edge, or they may have the same radius of curvature with a peripheral seal or gasket between them.

Preferably, the lenses are a new style of double lens in which the forward lens is convex and the rear lens is concave (the words "convex" and "concave" are used here meaning curved in both the horizontal and vertical directions), and the two lenses are bonded together along a single peripheral edge. These lenses may be formed with zero power in which the forward and rearward lenses are each constant thickness and different spherical radii of curvature to permit their edges to converge for bonding. Alternatively, a prescription may be ground into either lens. Special coatings can be provided on the adjacent faces of the two lenses which are protected from oxidation or scratching.

The present invention may be further provided with a cushion around the sealing area for increased sealing and protection.

Fixed positioning of the sports eyeglasses is accomplished by temple bars. The angular disposition of the general plane in which the frame lies may be further adjusted by providing adjusting connections at the temples. Each connection can be accomplished by a pivotal rack and pawl connection between the temple bars and the frame.

The frame includes a pair of temple bar stubs being attached to the frame at opposing ends. In one embodiment, a pair of temple bars are pivotally attached to each temple bar stub using a unique pivot pin and hole engagement configuration. Each temple bar includes a receiving segment having a pivot pin, rack receiving recess and an earpiece receiving channel. Thus, in this embodiment, the angle of the frame, with respect to the user's face, is dependant upon which particular tooth of the rack segment engages the pawl members.

The temple bars may also be provided with length adjustable earpieces and mastoid hooks to further aid in fitting the sports eyeglasses to the head and face of the user.

This invention is to provides protective eyewear for use in any type of weather.

Objects of the invention will become apparent upon reading the following specification and referring to the accompanying drawings.

BRIEF DESCRIPTION OF THE DRAWINGS

FIG. 5 is a partial side view of the right side of sports eyeglasses.

FIG. 6 is a cross section of the web taken along section 6—6 of FIG. 2, showing the position of the eye when worn by the wearer.

FIG. 7 is a front view of sports eyeglasses, having orbital sealing gaskets, with the lenses removed.

FIG. 8 is a cross section of the web taken along section 8—8 of FIG. 7, showing the position of the eye when worn by the wearer.

FIG. 9 is a front elevation view of another embodiment of sports eyeglasses having a single lens.

FIG. 10 is a front elevation view of another embodiment of sports eyeglasses.

FIG. 11 is a left side view of the temple bar and frame orbital adjusting connection.

FIG. 12 is a bottom view of the frame and frame orbital adjusting connection.

FIG. 13 is a cross section taken along section line 13—13 of FIG. 10.

DESCRIPTION OF THE PREFERRED EMBODIMENTS

Figure 1:
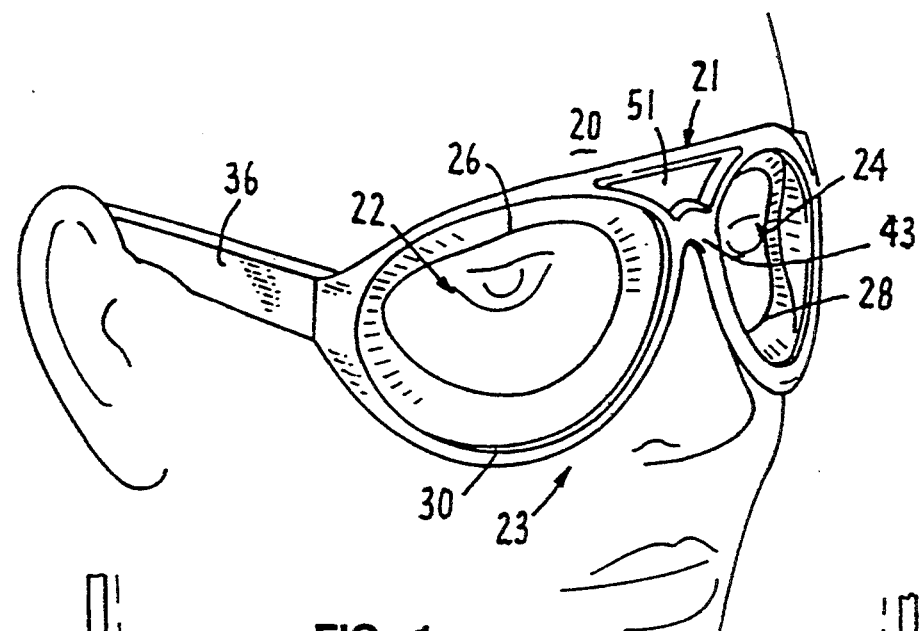
FIG. 1 is a front elevation view of sports eyeglasses shown worn by a user.
Figure 3:
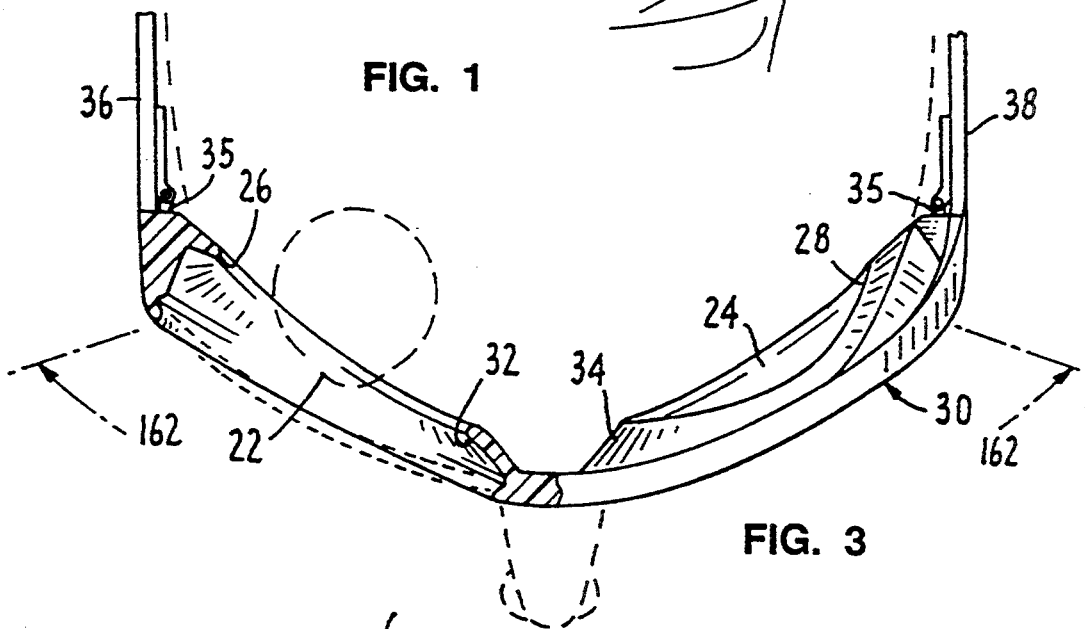
FIG. 3 is a cross section of FIG. 2 showing one embodiment of attachment of temple bar for sports eyeglasses.
Figure 2:
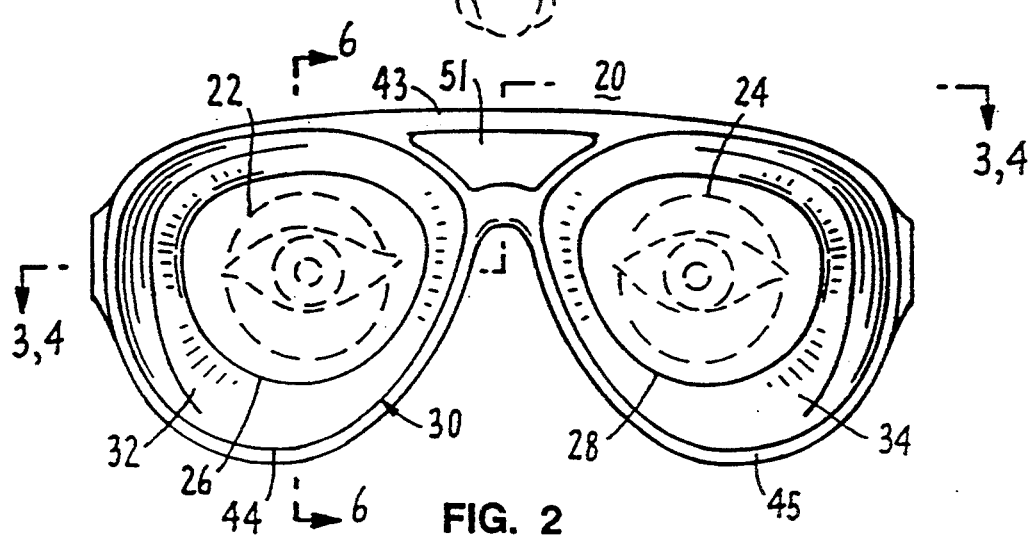
FIG. 2 is a front view of the sports eyeglasses of the present invention.
Figure 4:
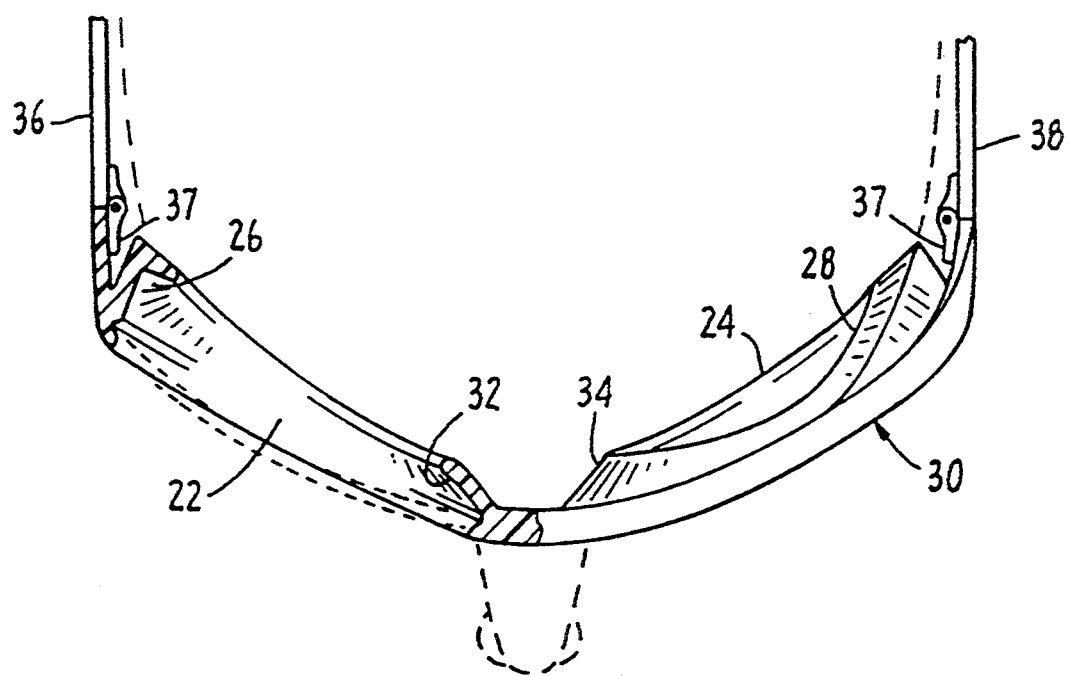
FIG. 4 is a cross section of FIG. 2 showing another embodiment of attachment of temple bar for sports eyeglasses.

Referring now to FIGS. 1–16, sports eyeglasses 20 are shown. Generally, sports eyeglasses 20 have a frame 21 which is attached to temple bars 36 and 38. Temple bars 36 and 38 are adapted to support the frame 21 on the wearer's head. In one embodiment, shown in FIG. 3, the temple bars 36 and 38 are attached to the frame 21 with 90 degree angle hinge 35. In FIG. 4, another embodiment, the frame 21 is extended to accommodate attachment of the temple bars 36 and 38 with 180 degree angle hinge 37. Temple bars 36 and 38 may further be provided with mastoid hooks (not shown) which enhance the securing capability of the temple bars 36 and 38.

The frame 21 is contoured in a wrap around configuration and has right lens opening 44 and left lens opening 45 in the lens support area 30. As shown in FIGS. 1–16, the frame 21 has a pair of eye apertures 22 and 24 which are adapted to be aligned with the wearer's eyes. Lens support area 30 surrounds the eye apertures 22 and 24. Each eye aperture 22 and 24 is provided with a sealing area 26 and 28, respectively, which surrounds the eye aperture 22 or 24, and which snugly fits against the skin of the wearer adjacent to the eye. Referring to FIGS. 3, 6 and 8, it is shown that the eye itself is forward of the sealing area 26 or 28 when the sports eyeglasses 20 are properly positioned on the face 23 of the wearer.

Webs 32 and 34 diverge from each sealing area 26 and 28, respectively to the lens support area 30 for enclosure of each eye without obstructing peripheral vision. Webs 32 and 34 attach to the interior side 42 of frame 21 at its divergent side. As shown in FIG. 3, the wearer is able to see at least 140 degrees and preferably over 160 degrees of peripheral vision with both eyes as indicated by the peripheral vision angle 162 in FIG. 4. The webs 32 and 34 may be provided with vent holes 73 to promote air circulation. The vent holes may be continuous with air grooves situated on the inner aspect of the lens support area but not evident from the front view. Vent holes 73 may be covered with cellular foam material 29 to further shield the user.

It can be seen that sports eyeglasses 20 are contoured to wrap around and closely fit the orbital area of the user which is the area barred by the user's nose, eyebrow and cheek bone. The exterior side 43 of sports eyeglasses 20 has a generally standard singles appearance, while the interior side 42, shown, for example, in FIG. 12, has more of a goggle-type appearance.

The lens support area 30 supports at least one lens. Typically, two lenses 46 and 47 are housed by the lens support area 30 in the frame 21. However, as shown in FIG. 9, a continuous lens which covers both right lens opening 44 and left lens opening 45 may be used. The lenses may be of single or double-walled construction, as illustrated in FIG. 13. In a double-walled construction, the lenses may have an airspace 76 and different radii of curvature. The double walled lenses may also have a single peripheral edge.

Between right lens opening 44 and left lens opening 45 there is positioned a ram air intake 51 for directing filtered air into the eye chamber through the vent holes. Referring to FIG. 10, ram air intake 51 may be covered with ram air intake filter cover 52. Construction of ram air intake filter cover 52 typically can be from a thin breathable cellular foam material.

Alternatively, ram air intake 51 can be circumferentially covered on the inner side so that the ram air intake 51 appears to be open when viewed from the exterior side 43 of the sports eyeglasses 20. With the circumferential covering of ram air intake 51, intake air passing through is directed venturily down through those the vents 73 enclosed by the circumferential covering in the webs 32 and 34 to enhance ventilation and decrease the formation of mist on the lenses 46 and 47 of the sports eyeglasses 20.

FIGS. 10–16 show a further embodiment of the present invention. In the embodiment depicted in FIGS. 10–16, a pair of the temple bars 36 and 38 meet temple bar stubs, right temple bar stub 48 and left temple bar stub 49, which are attached and extend outward from opposite ends of the frame 21. Both temple bar stubs 48 and 49 have upper and lower pivot pin engagement holes 50 for engaging the temple bars 36 and 38. For the sake of illustration, only the left temple bar 38 is shown in its entirety. However, it should be apparent that right temple bar 36 is identical in construction and is a mirror image of left temple bar stem 53. Left temple bar 38 has left rack arm 54 pivotally attached to left temple bar stub 49 via pivot pin 56 and lower pivot pin engagement hole 50. The left rack segment 55 of left rack arm 54 is slidably received within left rack arm receiving recess 58 in left receiving segment 57. Left receiving segment 57 is also provided with a pivot pin 56 which pivotally engages the upper pivot pin engagement hole 50 in left temple bar stub 49.

Left pawl arm 59 is attached within left rack arm receiving recess 58 and generally has a left resilient pawl member 61 attached at one end and includes a left pawl or protuberance 60 at its other end for engaging left rack segment 55. Advantageously, the opening in left rack arm receiving recess 58 is sized to closely receive left rack arm 55. Left resilient pawl member 61 bends downwardly to allow the adjustable movement. The angle which frame 21 makes with respect to right and left temple bar 36 and 38, is dependent upon which particular tooth of rack segment 55 with which pawls 60 are engaged.

The back portion of left receiving segment 57 is also provided with left earpiece receiving channel 62 with slidably and frictionally engages channel member 64. Channel member 64 is colinearly attached to left earpiece 63, thereby providing a length adjustable earpiece 63 for sports eyeglasses 20.

Again, a right orbital adjusting connection is similarly constructed to the left orbital adjusting connection previously explained, and is shown best in FIG. 12.

Figure 16:
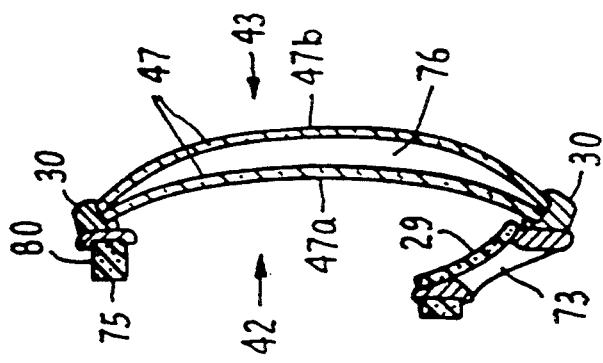
FIG. 16 is an analogous view to that of FIG. 13 showing another embodiment of the sports eyeglasses having perspiration channel in the upper portion of the orbital sealing gasket.
Figure 14:
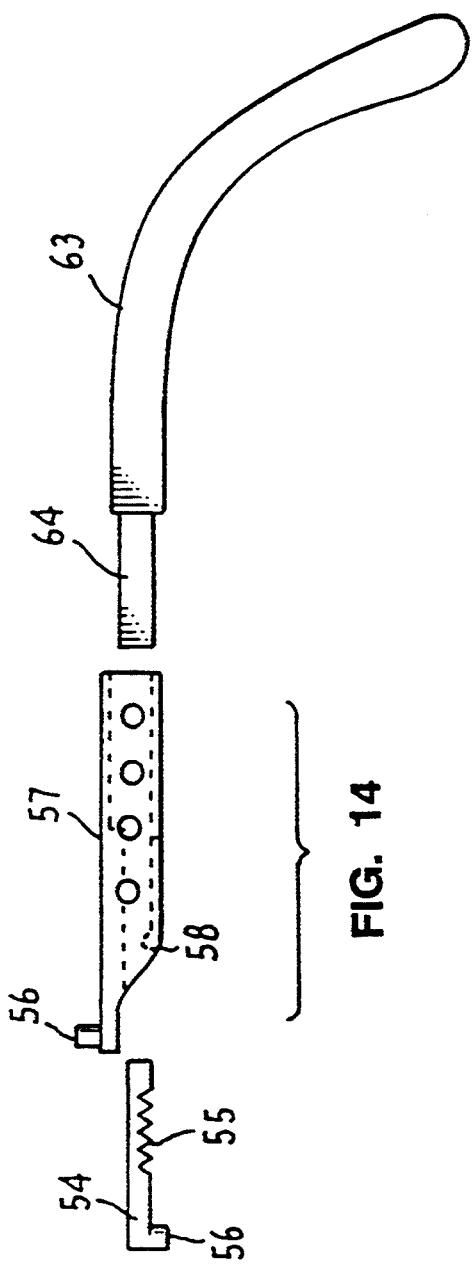
FIG. 14 is an exploded side view of the left temple bar.
Figure 15:
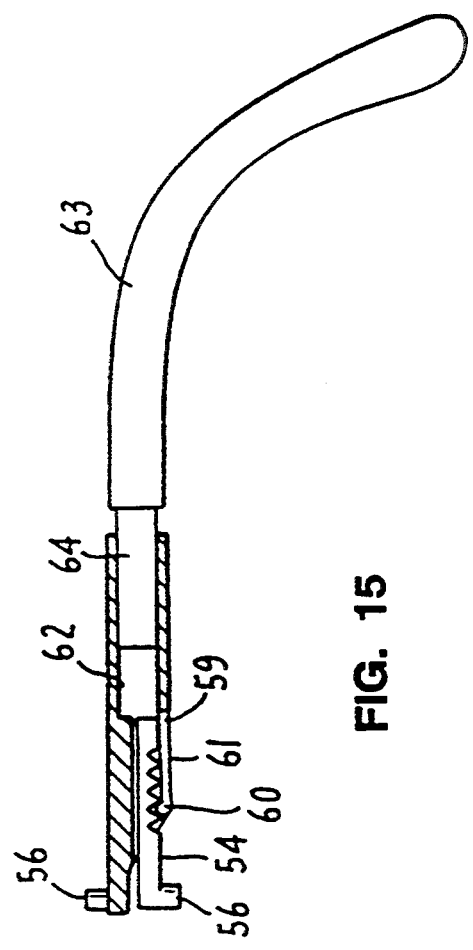
FIG. 15 is partial cutaway assembled view of FIG. 14.

FIG. 16 shows a second embodiment of sports eyeglasses 20 which includes a perspiration channel 80 in the upper portion of orbital sealing gasket 75. Orbital sealing gasket 75 may be added to sealing area 26 and 28 to enhance the seal and/or provide a facial cushion. Advantageously, the upper portion of orbital sealing gasket 75 is manufactured of a non-porous foam cushion material so as not to absorb perspiration. The orbital sealing gasket 75 could be manufactured from any suitable material and/or in a compressible accordion fashion to provide a tight seal against the face of the user.

Perspiration channel 80 runs along the top of the of the frame 21 such that perspiration from the forehead of the user is directed to the lateral sides of sports eyeglasses 20, away from the face and eyes of the user.

Other modifications include addition of a nosepiece, enlarging the upper and/or lower portions of the lens frame and corresponding lenses to enhance superior and inferior vision. This is especially desirable in a sport such as bicycling where the user head is oftentimes face down, forcing the user to look out the top portion of the lens.

Additionally, to frame 21 there may be added apertures to provide for increased venting through the interior of the sports eyeglasses 20. A further modification can include the insertion of grooves and/or a metal rod 49 at the interior of the frame 21 across the nose of the wearer for flexibility and fit.

While there is shown and described the present preferred embodiment of the invention, it is to be distinctly understood that this invention is not limited thereto but may be variously embodied to practice within the scope of the following claims.

I claim:

1. A protective eyewear device for use in sports and the like comprising: a semi-rigid frame having
   a pair of eye apertures adapted to be aligned with a wearer's eyes,
   a sealing area surrounding each aperture adapted to engage the wearer's skin adjacent to the eye, said sealing area including a sealing gasket with a perspiration channel disposed along its upper portion for directing perspiration away from the eyes and face of the wearer,
   a lens support area surrounding each aperture with the sealing areas and lens support areas positioned to permit at least about 140 degrees peripheral vision with both eyes,
   a web diverging from each sealing area to the adjacent lens support area in every direction to enclose the eye without obstructing the peripheral vision, and including ventilating apertures therethrough;
   a pair of temple bar means attached to the frame and adapted to support the frame on the wearer's head; and,
   a curved lens means mounted to the lens support areas to cover the apertures, said curved lens means including at least one substantially rigid curved lens formed from two lens elements which are transparent to visible light and which are bonded together along a single peripheral edge to fix the orientation of the two lens elements relative to each other and to form an external front surface which is convex, an external rear surface which is concave, and two facing internal surfaces at least a part of which are spaced apart from each other.

2. The eyewear of claim 1 wherein one curved lens covers each aperture.

3. The eyewear of claim 1 wherein said lens elements have different radii of curvature.

4. The eyewear of claim 1 wherein said lens elements are both constant thickness spherical lenses.

5. The eyewear of claim 1 further including a sealing gasket along the peripheral edge between said lens elements.

6. The eyewear of claim 1 wherein said space between said internal surfaces of said lens elements contains air.

7. The eyewear of claim 1 wherein at least one of said internal surfaces are coated.

8. The eyewear of claim 4 wherein said coating is antireflective.

9. The eyewear of claim 7 wherein said coating is hydrophilic.

10. The eyewear of claim 1 wherein at least one lens element is ground to change the power of the lens to correct the vision of the wearer.

11. A protective eyewear device for use in sports and the like comprising:
   a semi-rigid frame having
      a pair of eye apertures adapted to be aligned with a user's eyes,
      a sealing area surrounding each aperture adapted to engage the wearer's skin adjacent to the eye,
      a lens support area surrounding each aperture with the sealing areas and lens support areas positioned to permit at least about 140 degrees peripheral vision with both eyes,
      a web diverging from each sealing area to the adjacent lens support area in every direction to enclose the eye without obstructing the peripheral vision, said web including ventilating apertures covered with permeable foam for substantially preventing the passage of wind and foreign material therethrough, said web further having a foam means contoured to partially cover the web so that air is trapped and directed through the ventilation apertures to increase air circulation;
   a pair of temple bar means attached to the frame and adapted to support the frame on the wearer's head; and,
   a substantially rigid, curved lens mounted to each lens support area to cover each aperture, each lens formed from two curved lens elements which are transparent to visible light and which are bonded together along a single peripheral edge to fix the orientation of the lens elements relative to each other and to form an external lens front surface which is convex, an external rear lens surface which is concave, and two facing internal surfaces at least a portion of which are spaced apart from each other.

12. The eyewear of claim 11 wherein said lens elements have different radii of curvature.

13. The eyewear of claim 11 wherein said lens elements are both constant thickness spherical lenses.

14. The eyewear of claim 11 further including a sealing gasket along the peripheral edge between said lens elements.

15. The eyewear of claim 11 wherein said space between said internal surfaces of said lens elements contains air.

16. The eyewear of claim 11 wherein at least one of said internal surfaces are coated.

17. The eyewear of claim 16 wherein said coating is antireflective.

18. The eyewear of claim 16 wherein said coating is hydrophilic.

19. The eyewear of claim 11 wherein said lenses are zero power.

20. The eyewear of claim 11 wherein at least one of said lens elements is ground to correct the vision of the wearer.

21. A rigid, curved lens transparent to visible light for use in an eyeglass frame having a pair of eye apertures adapted to be aligned with a user's eyes, a sealing area surrounding each aperture adapted to engage the wearer's skin adjacent to the eye, a lens support area surrounding each aperture, a web diverging from each sealing area to the adjacent lens support area in every direction to enclose the eye without substantially obstructing the peripheral vision, said web including ventilating apertures covered with permeable foam, said web further having a foam means contoured to partially cover the web whereby air is trapped and directed through the ventilation apertures to increase air circulation, and a pair of temple bar means attached to the frame and adapted to support the frame on the wearer's head, said lens comprising:
   a first spherical lens element transparent to visible light and having a convex first surface, a concave second surface opposite said first surface, and a first radius of curvature;
   a second spherical lens element transparent to visible light and having a convex first surface, a concave second surface opposite said first surface, and a second radius of curvature which is different from the first radius of curvature;
   said first and second lens elements bonded together along a single peripheral edge to fix the orientation of the first lens element relative to the second lens element, whereby at least a portion of said second surface of said first lens element is spaced apart from and faces said first surface of said second lens element, the space between the first and second lens element containing a gas; whereby when said lens is mounted in the lens support area, the first surface of the first lens element faces away from the wearer and the second surface of the second lens element faces towards the wearer;
   and wherein at least one of said second surface of said first lens element and said first surface of said second lens element is coated.

22. The lens of claim 21 wherein said gas is air.

23. The lens of claim 21 wherein the coating is antireflective.

24. The lens of claim 21 wherein the coating is hydrophilic.

25. The lens of claim 21 wherein the lens has zero power.

26. The lens of claim 21 wherein at least one of the lens elements is ground to correct the vision of the wearer.

* * * * *